(12) United States Patent
Heitfeld et al.

(10) Patent No.: US 6,432,661 B1
(45) Date of Patent: Aug. 13, 2002

(54) METHOD FOR QUANTITATING ORGANIC PERACID USING CATALASE

(75) Inventors: Fred A. Heitfeld, Castro Valley; Susan A. Anderson, Menlo Park, both of CA (US)

(73) Assignee: The Clorox Company, Oakland, CA (US)

( * ) Notice: Subject to any disclaimer, the term of this patent is extended or adjusted under 35 U.S.C. 154(b) by 0 days.

(21) Appl. No.: 08/318,574

(22) Filed: Oct. 5, 1994

Related U.S. Application Data

(63) Continuation of application No. 07/942,121, filed on Sep. 8, 1992, now abandoned, which is a continuation of application No. 07/575,095, filed on Aug. 30, 1990, now abandoned, which is a continuation of application No. 07/508,331, filed on Apr. 11, 1990, now abandoned, which is a continuation of application No. 07/223,502, filed on Jul. 25, 1988, now Pat. No. 4,957,063.

(51) Int. Cl.$^7$ ................................................ C12Q 1/30
(52) U.S. Cl. ......................................... 435/27; 435/192
(58) Field of Search .............................. 435/4, 27, 192; 252/99, 94, 95, 186.38, 186.41, 186.42, 186.43, 186.1; 436/135

(56) References Cited

U.S. PATENT DOCUMENTS

| | | | |
|---|---|---|---|
| 3,677,903 A | | 7/1972 | Bittner ................. 195/103.5 R |
| 4,338,210 A | | 7/1982 | Clements et al. .............. 252/96 |
| 4,421,668 A | | 12/1983 | Cox et al. ............... 252/174.12 |
| 4,427,566 A | * | 1/1984 | Clements ..................... 252/102 |
| 5,108,457 A | * | 4/1992 | Poulose .......................... 8/111 |
| 5,296,161 A | * | 3/1994 | Wiersema et al. ...... 252/186.38 |
| 5,364,554 A | * | 11/1994 | Stanislowski ........... 252/186.38 |

FOREIGN PATENT DOCUMENTS

| | | | |
|---|---|---|---|
| DE | 3806403 | 9/1989 | ......... C07C/179/10 |
| EP | 310952 | 4/1989 | ......... C07C/179/10 |
| EP | 359087 | 3/1990 | ............ C11D/3/38 |

OTHER PUBLICATIONS

Siggia et al., "Quantitative Organic Analysis via Functional Groups", Krieger Publishing Co. Inc., (1988); p. 344.
Swern, "Organic Peroxides", vol. 1, Wiley & Sons, Inc. (1970), pp. 900–905.
Johnson & Siddiqi, "The Determination of Organic Peroxides", Pergamon Press (1970), pp. 15–24; 43–59; 70–74; 83–97.
Bio. Abs.; vol. 75, pp. 6642–6643 (1983), reporting on Rep. Natl. Food Res. Inst. (Tokyo), vol. 39, pp. 43–47 (1982).
Anal. Biochem., vol. 76, pp. 184–191 (1976).
Anal. Biochem., vol. 193, pp. 204 211 (1991).
Analyst, vol. 113, pp. 1477–1479 (1988).
S.N. Lewis, "Peracid and Peroxide Oxidations," to AL In: *Oxidation* (1969) Marcel Dekker, pp. 213–257.
R.M. Johnson et al., *The Determination of Organic Peroxides* (Pergamon, 1970) pp. 1–27.
H. Aebi, "Catalase," in: Methods of Enzym. Analysis, vol. 2, pp 673–682 (1971) Frew et al., "Structural and Functional Properties of Peroxidases and Catalases," in: Advances in Inorganic and Bioinorganic Mechanisms, vol. 3, p. 175 (1984).

* cited by examiner

*Primary Examiner*—Ralph Gitomer
(74) *Attorney, Agent, or Firm*—Joel J. Hayashida

(57) ABSTRACT

The invention provides an improved procedure for the precise quantitation of organic oxidants in a solution with hydrogen peroxide in which the peroxide is removed by the addition of catalase to scavenge the same. Surprisingly, the catalase does not affect the organic oxidant, and the procedure can accurately quantitate even minute amounts of the organic oxidant. The inventive method is especially effective in quantitating peracid generated enzymatically, although it can be used for chemically generated organic oxidants.

20 Claims, 2 Drawing Sheets

FIG._1

METHOD FOR QUANTITATING ORGANIC PERACID USING CATALASE

This is a continuation, of application Ser. No. 07/942,121, filed Sep. 8, 1992, now abandoned, which is a continuation of Ser. No. 07/508,331 filed Apr. 11, 1990 abandoned which is a continuation of Ser. No. 07/575,095, filed Aug. 30, 1990, abandoned, which is a continuation of Ser. No. 07/223,502 filed Jul. 25, 1988, now U.S. Pat. No. 4,957,063.

BACKGROUND OF THE INVENTION

1. Field of the Invention

This invention relates to a method for quantitating organic oxidants, and is especially useful in detecting low amounts of peracid as low as about 0.3 ppm A.O.(parts per million active oxygen) in systems containing high amounts of hydrogen peroxide.

2. Brief Description of Related Art

Standard titration techniques have been developed for the quantitative determination of organic oxidants, such as organic peracids. S. N. Lewis, "Peracid and Peroxide Oxidations," in: *Oxidation* (Marcel Dekker, 1969).

Various other quantitative assays have been developed, e.g., electrochemical determination, but these prior art systems suffer from the inability to detect small quantities of organic oxidants in the presence of hydrogen peroxide.

Cox et al, U.S. Pat. No. 4,421,668, discloses a liquid bleach composition containing a hydrogen peroxide precursor comprising an alcohol oxidase and, as the substrate for the oxidase, a specific alcohol. The patent mentions that within the cell-free extract of alcohol oxidase, there is some catalase naturally present as a contaminant (column 5, lines 26–32.) Cox also notes that it is preferred to limit the amount of catalase present in the claimed liquid composition.

Clements et al, U.S. Pat. No. 4,338,210, discloses a low temperature bleach composition comprising a peracid precursor system, and a source of bromide ions. The patent notes that if there is an excess of sodium perborate present in the peracid precursor system, such excess amounts can be scavenged by including a discrete quantity of catalase (column 6, lines 14–59).

However, none of the prior art discloses, teaches or suggests that catalase is an efficient scavenger or quenching agent for hydrogen peroxide, without affecting the organic oxidant being assayed. Further, nothing in the prior art discloses, teaches or suggests that catalase may act as a selective oxidant for hydrogen peroxide. Moreover, none of the prior art discloses, teaches or suggests that a quantitative method using catalase as a scavenging or quenching agent for hydrogen peroxide can detect very low quantities of organic oxidant against a large background of hydrogen peroxide.

SUMMARY OF THE INVENTION AND OBJECTS

The invention relates to a method for quantitating organic oxidants in which an amount of catalase is introduced into a solution containing the organic oxidant and hydrogen peroxide, the amount being sufficient to decompose the hydrogen peroxide. Thereafter, the organic oxidant is quantitated by known methods.

It is therefore an object of this invention to provide a method for quantitatively determining organic oxidants present in a solution.

It is a further object of this invention to provide a method for detecting very low quantities of organic oxidants in a solution.

It is also an object of this invention to provide a quantitative assay which can detect low amounts of organic peracids in a solution in the presence of a high background of hydrogen peroxide.

It is yet another object of this invention to provide a method of quantitating organic oxidants in which background hydrogen peroxide can be quenched or scavenged without significantly affecting the organic oxidants contained therein.

DETAILED DESCRIPTION OF THE PREFERRED EMBODIMENT

Figure 1:
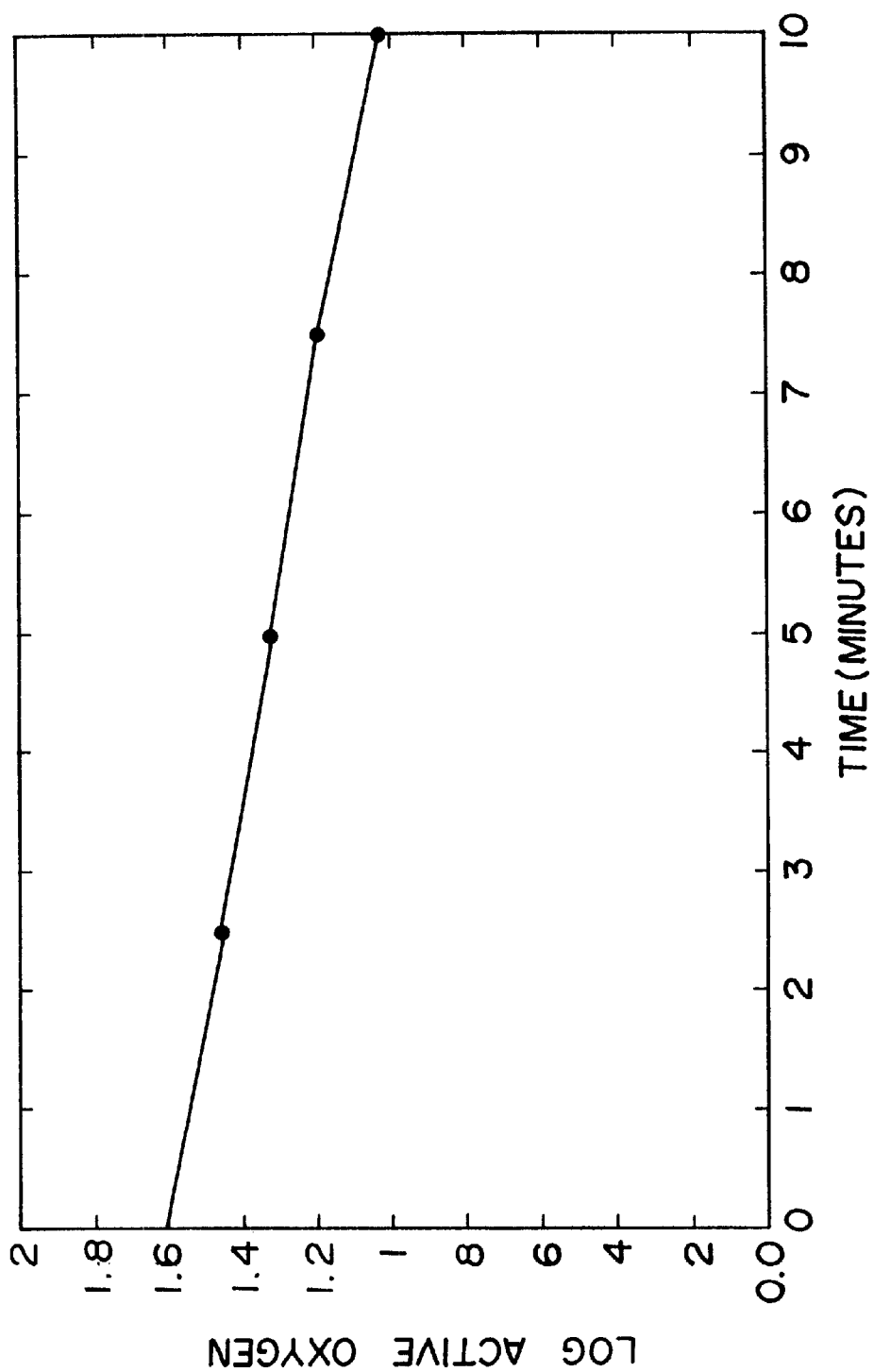
FIG. 1 is a graph depicting hydrogen peroxide decomposition mediated by catalase.

The invention relates to a method for quantitating organic oxidants comprising:

introducing, into a solution containing an organic oxidants and hydrogen peroxide, an amount of catalase sufficient to decompose hydrogen peroxide in said solutions; and quantitating said organic oxidant.

In the synthesis of new, organic oxidants, there are numerous techniques available to ascertain qualitatively the identity of such new organic oxidants, e.g., nuclear magnetic resonance spectroscopy (NMR) and infra-red spectroscopy (IR).

However, in the quantitative assay of organic peracids, resort is typically made to standard techniques such as titration, or high pressure liquid chromatography (HPLC). As an example of HPLC, the method described by Isaksson et al., "Reaction Detector for Liquid Chromatography with Electrochemical Generation and Detection of Excess Bromide", in: *Journal of Chromatography*, Volume 324, pages 333–342 (1985), has been modified to determine quantities of peracid contained in solution. In the adaptation, a mixture of materials including a peracid can be separated on a silica gel-packed column. A quantity of potassium iodide (KI) is added to the chromatographic solvent after the peracid is separated in the column. The KI is oxidized to iodine ($I_3^-$) by the peracid and measured coulometrically. This measurement of iodine is an indirect measure of the peracid since the generated signal is stoichiometrically related to the peracid which has been reduced. This adapted technique has proved to be quite useful in quantitating peracids generated from the reaction of hydrogen peroxide and a peracid precursor, also known as a bleach activator.

Organic peracids have been generated by the reaction of hydrogen peroxide and various substituted glycerides in the presence of lipase enzymes (See e.gs., European Patent Applications EP 253,487 and EP 268,456, the disclosures of which are incorporated herein by reference). Generation of peracid by this technique is known as "enzymatic perhydrolysis". Because these reactions are typically conducted with substoichiometric amounts of enzyme in combination with the appropriate substrate (e.g., triglyceride), in the presence of a comparatively overwhelming amount of hydrogen peroxide, the detection of generated peracid is usually quite problematic. The large excess of hydrogen peroxide can interfere in the quantitation of the generated peracid when using the thiosulfate titration method. Common methods to distinguish peracid from hydrogen peroxide such as chilling the analysis mixture to retard $H_2O_2$ reactivity or selectively accelerating the $H_2O_2$ reaction (e.g., by molybdate catalyst) are not effective at high $H_2O_2$ concentrations. Secondly, because lipase works at a phase interface, the generation of peracid may be localized. Further, because in the presence of $H_2O_2$ peracid may have a relatively short half-life, it may be difficult to detect and quantify such generated peracid.

Therefore, there exists a felt need for an accurate quantitation technique for organic oxidants in which large quantities of hydrogen peroxide can be quenched or scavenged to prevent interference with the quantitative determination. By "blanking out" such large amounts of hydrogen peroxide, detection of discrete amounts of organic oxidants, such as enzymatically generated peracids, is surprisingly, greatly facilitated, without having to resort to separation techniques which may affect the accuracy of the quantitation.

However, this system can also be adapted for use in quantitating peracid generated in relatively abundant quantity, e.g., when an efficient bleach activator or peracid precursor is reacted with a source of hydrogen peroxide. As an example of such bleach activators, which are typically esters, see, Fong et al, U.S. Pat. No. 4,778,618, the disclosure of which is incorporated herein by reference. As can be seen in Fong, peracid is typically generated when an organic ester and hydrogen peroxide are combined. The archetypical reaction is:

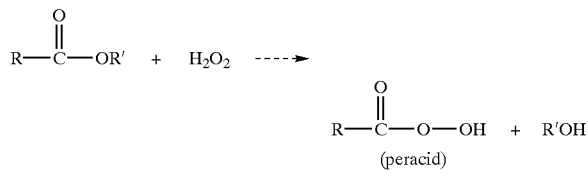

The Method

The basic method utilizes the standard sodium thiosulfate titration method depicted in Lewis, "Peracid and Peroxide Oxidations", in Oxidation (Marcel Dekker, 1969). In this technique, the total active oxygen content of a solution (including hydrogen peroxide and any organic oxidants present) may be determined by combining the oxidants in a solution with an excess of potassium iodide to form iodine ($I_3^-$) which is then titrated with standardized sodium thiosulfate. Qualitatively, the presence of $I_3^-$ will yield a yellow color. Quantitatively, on the other hand, titration with sodium thiosulfate towards a colorless end product is necessary to determine, indirectly, the total quantity of oxidant present. Additionally, since towards the end of the titration, the endpoint is quite difficult to see, a few drops of starch indicator are usually added when nearly all of the $I_3^-$ has been titrated.

In one alternate technique to determine organic oxidants in $H_2O_2$, a so-called "cold thiosulfate" technique is used in this variation, the solution is chilled on ice. Then potassium iodide is added to react with oxidants. When chilled, the reaction of $H_2O_2$ with iodide will be retarded relative to the rate of the peracid/iodide reaction. Thus, peracid is preferentially titrated. Once all the peracid has been titrated, then a catalyst, such as ammonium molybdate, can be added to accelerate the $H_2O_2$/iodide reaction. This is then titrated with $Na_2S_2O_3$ to quantitate the $H_2O_2$ content.

It has been advantageously found that the potassium iodide reaction works best in an acidic medium. Therefore, a discrete amount of an acid is added. Examples of typical acids would be sulfuric acid, hydrochloric acid, and most preferably, acetic acid. The use of acetic acid has been found to eliminate some background interference due to air oxidation in the detection of small quantities of organic oxidants. See, Johnson and Siddiqi, *The Determination of Organic Peroxides,* pp.15–26 (1970), incorporated herein by reference.

As previously mentioned, peracid generated by enzymatic perhydrolysis has proven difficult to quantitate. Generally speaking, other methods suffer because of the difficulty in distinguishing peracid from hydrogen peroxide. Moreover, in enzymatic perhydrolysis, significant peracid generation can be as low as 0.5 parts per million active oxygen (ppm A.O.). Active oxygen is a significant measure and is defined herein as an attribute of compounds having a peroxide linkage —O—O— in which one oxygen atom is active and capable of oxidizing $I^-$ to $I_3^-$. See, D. Swern, *Organic Peroxides,* Vol. I (1970), incorporated herein by reference.

In enzymatic perhydrolysis, an esterolytic enzyme, e.g., esterase, lipase (see E.P. 253,487 and 268,456, incorporated herein by reference) or a protease (see co-pending U.S. patent application Ser. No. 07/243,331, of A. G. Stanislowski et al., filed Sep. 6, 1988, now U.S. Pat. No. 5,364,554 entitled "Proteolytic Perhydrolysis System and Method of Use for Bleaching", incorporated herein by reference), is combined with a source of hydrogen peroxide and a substrate, therefor, which, in combination with the enzyme and hydrogen peroxide, will produce peracid. The substrate is a chemical which, in combination with the hydrogen peroxide and the selected enzyme generates at least a significant amount of peracid of greater than about 0.5 ppm A.O. The enzymatically generated peracid is distinct from chemical perhydrolysis, which is the reaction of a bleach activator (typically, an ester) with hydrogen peroxide to produce peracid. Generally, the substrate and the hydrogen peroxide will not produce any discernible peracid in the absence of the enzyme.

Exemplary substrates include:
(a) when the enzyme is a lipase or esterase:
  (i) glycerides having the structure

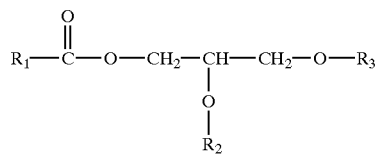

wherein $R_1=C_{1-12}$, and $R_2$,

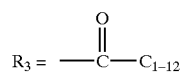

or H;
(ii) an ethylene glycol derivative or ethoxylated ester having the structure

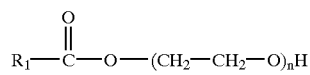

wherein n=1–10 and $R_1$ is defined as above; and (iii) a propylene glycol derivative or propoxylated ester having the structure

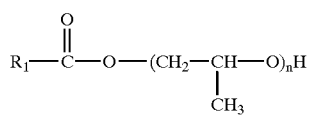

wherein n and $R_1$ are defined as above.

Within the preferred structures referred to immediately above, $R_1$ is more preferably $C_{6-10}$ and most preferably $C_{8-10}$, $R_2$ and $R_3$ have more preferably a $C_{6-10}$ alkyl group and most preferably a $C_{8-10}$ alkyl group, or H.

The use of glycerides, especially diglycerides and triglycerides, is particularly preferred when the esterolytic enzyme is lipase or esterase, since diglycerides and triglycerides have more than one acyl group which can yield peracid when combined with the selected enzyme in the presence of hydrogen peroxide. Thus, glyceride may be particularly effective in achieving very efficient perhydrolysis in the presence of the lipase/esterase and a source of hydrogen peroxide.

The glyceride substrate is characterized by carboxylic acid moieties having from about one to eighteen carbon atoms. Lower molecular weight glycerides derived from e.g., acetic acid, will be liquid. Thus, extra processing steps may be necessary in preparing such glycerides for inclusion in a dry product, such as a laundry detergent. While higher molecular weight glycerides, such as $C_{6-10}$ glycerides will also be liquid, they are advantageous because they will produce surface active peracids, which are effective at surface bleaching. Mixtures of varying chain length glycerides are also preferred.

Exemplary triglyceride substrates are triacetin, trioctanoin, trinonanoin, tridecanoin, and tristearin. Trioctanoin is especially preferred.

When a glyceride is the substrate, however, it is difficult to quantitate the peracid generated due to the physical form of the substrate. The preferred glycerides are often insoluble or sparingly soluble in water. Thus, in order to be acted on by the enzyme, glycerides may have to dispersed using surfactant or emulsion systems. Common detergent surfactants can be utilized. Anionic, cationic, nonionic and amphoteric surfactants, and mixtures thereof, can be utilized. An exemplary surfactant is sodium dodecyl sulfate ("SDS") which has been commonly used to formulate detergents. See also, Kirk-Othmer, *Encyclopedia of Chemical Technology*, Third Edition, Vol. 22, pages 347–387, and *McCutcheon's Detergents and Emulsifiers*, North American Edition, 1983, which are incorporated herein by reference. Polyvinyl alcohol ("PVA") is another preferred emulsifier. It is preferred that such PVA's be of relatively low molecular weight (e.g., generally less than about 100,000 M.W.). Bile salts and water soluble gums can be added as dispersing aids.

A solvent or other emulsifier may be needed to disperse/solubilize the emulsion to facilitate quantitation. Solvents, such as ethanol, propanol, chloroform, and any other organic solvent which does not interfere with, or participate in, the perhydrolysis reaction or in the titration reactions, can be utilized. Ethanol has been found to be preferred.

Other exemplary substrates include:
(b) when the enzyme is a protease:

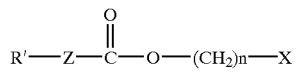

wherein $R'=C_{1-10}$ alkyl; $Z=O$, $(CH_2CH_2O)_m{}^-$,

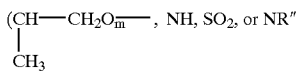, $NH$, $SO_2$, or $NR''$ (wherein m=0–10 and
$R''$=phenyl or $C_{1-4}$ alkyl); n=2–10; X=OH, —OR$\Delta$ or —NR''$_2$; and X may be pendent on or terminate the hydrocarbyl chain.

Exemplary substrates here include $C_{1-10}$ alkyl esters, e.gs, methyl octanoate, methyl acetate; substituted esters, e.gs., methylmethoxyacetate, (2-hexyloxyethoxy) acetic acid, (2-hydroxypropyl) ester, 2-hydroxypropyloctanoate.

The inventive titration technique can also be applied to the quantitative of peracids generated chemically, e.g., via an effective bleach activator reacting with hydrogen peroxide. Exemplary activators are disclosed in Farr et al., U.S. Pat. No. 4,900,469, Zielske et al., U.S. Pat. No. 4,859,800, Fong et al., U.S. Pat. No. 4,814,110, Steichen et al., U.S. Pat. No. 4,790,952, Fong et al., U.S. Pat. No. 4,778,618, Mitchell et al., U.S. Pat. No. 4,772,290, and Zielske et al., U.S. Pat. No. 4,735,740 all of common assignment and incorporated herein by reference.

The organic activator came broadly defined herein as either (a) an organic compound, such as an ester, which reacts with hydrogen peroxide to form a corresponding peracid; or (b) a substrate for an esterolytic enzyme, which, in the presence of the designated enzyme and hydrogen peroxide produces peracid enzymatically.

Surface active activators are preferred since they will produce peracids which will work at a fabric surface when, for example, the organic activator and a hydrogen source are combined for fabric bleaching products.

Catalase

The $H_2O_2$ quenching agent is catalase. Catalase is a large enzyme (244,000 to 250,000 molecular weight) which catalyzes the rapid decomposition of hydrogen peroxide into water and oxygen.

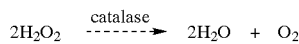

Catalase is manufactured by plants, animals and microorganisms and has been shown to be effective at decomposing hydrogen peroxide (from dry bleaches) at pH 7.0. A commercial source of catalase is Sigma bovine liver catalase. See, H. Äbi, "Catalase," in: *Methods of Enzymatic Analysis*, Vol. 2 ed. H. Bergmeyer, pp. 673–682 (1971), incorporated herein by reference; and Frew and Jones, "Structural and Functional Properties of Peroxidases and Catalases," in: *Advances in Inorganic and Bioinorganic Mechanisms*, Vol. 3, p. 175 (1984), incorporated herein by reference.

The units of activity for catalase was measured at 1900 units/mg solid where 1 unit decomposes 1.0 $\mu$mole of $H_2O_2$ per minute at 25° C., while the $H_2O_2$ concentration falls from 10.3 to 9.2 $\mu$moles/ml in the reaction mixture.

It has been found that an effective amount of catalase in the invention is the number of units that, for a 10 ml sample of $H_2O_2$ (800 ppm A.O.), will completely decompose, oxidize or quench within three minutes at room temperature (about 21° C.) at a pH of about 10.5, without substantially affecting any peracid present in the sample. The units of activity are measured in units per ml of solution (U/ml). While it has been preferably found that 843 U/ml of sample of catalase are effective, in fact, a half, to a tenth, of that amount is considered to be similarly effective.

On the other hand, excessive amounts of catalase should also be avoided. Excessive amounts are those which would provide a preferentially oxidizible substrate for the generated peracids. In certain quantities, catalase, similar to other proteins, would no longer act solely as a catalyst, but would be "recognized" as an oxidizible substance by the peracid.

Because of catalase's known propensity to preferentially decompose $H_2O_2$, applicants experimented with catalase to determine whether it would similarly oxidize organic oxidants.

In the Experimental section which follows, the discoveries that catalase will react with $H_2O_2$, but not react with peracid, are described, along with the manual and automated titration methods for quantitating peracid.

Experimental

In the following experiments, A.O. determinations are to be made. Thus, in Example I, A.O. calculations are demonstrated for hydrogen peroxide, sources thereof, and for organic oxidants.

EXAMPLE I

Active Oxygen (A.O.) Determination

A. Iodometric Titration for ppm A.O.
  1. Equation for the titration of $H_2O_2$:

$$H_2O_2 + 2I^- + 2H^+ \rightarrow I_2 + 2H_2O\ 2S_2O_3^{-2} + I_2 \rightarrow S_4O_6^{-2} + 2I^-$$

2. Calculation of active oxygen:

$$\text{ppm A.O.} = \frac{(NS_2O_3^{-2})(\text{Volume } S_2O_3^{-2}1)(\text{eq.wt.O}) \times 10^6}{(\text{wt. of sample g.})}$$

3. Reagents

The following reagents were assembled. All solutions indicate prepared with deionized, distilled water. All measurements are in percent (wt. %), unless otherwise indicated.
  1. 0.01N aqueous sodium thiosulfate ($Na_2S_2O_3$. Standardized and stored in a brown bottle.
  2. 10% (wt/vol) aqueous potassium iodide (KI). Stored in a brown bottle away from light.
  3. 10% (vol/vol) $H_2SO_4$
  4. Starch indicator. (Preparation is by adding 10.1±0.1 gms. potato starch (J. T. Baker 4006, reagent grade) and adding to 15 ml distilled or deionized water, forming a smooth paste. Then pour starch paste into 1 liter boiling distilled or deionized water and boil 15 minutes with stirring. Cool to 49°–54° C. and add 1.2–1.3gms. salicylic acid (J. T. Baker 0300,reagent grade). Pour into stoppered bottle, cap tightly and store.)
  5. 0.1N potassium iodate ($KIO_3$) (J. T. Baker Dilut-it, Cat.#4676)

4. Standardization of Sodium Thiosulfate
    a. Preparation. 2.0 ml of 0.1N $KIO_3$ were used as a primary standard. The $KIO_3$ was diluted with 20 ml distilled water and acidified with 5 ml of 10% $H_2SO_4$. 10 ml of 10% KI was added and the sample was titrated with $Na_2S_2O_3$ until it became light yellow. At this point, 5 drops of starch indicator were added and the titration was continued until the clear endpoint was reached.
    b. Calculation.

$$\text{Normality (N) } Na_2S_2O_3 = \frac{\text{ml } KIO_3(N\ KIO_3)}{\text{ml } Na_2S_2O_3}$$

5. Manual Oxidant Titration
    To 10 g of sample, 10 ml of 10% KI and 10 ml of 10% $H_2SO_4$ were added. The sample was then titrated with $Na_2S_2O_3$ until it became light yellow. At this point, 5 drops of starch indicator were added and the titration was continued until the colorless endpoint was reached.

EXAMPLE II

Catalase Activity

A. Reagents
  1. 0.01M hydrogen peroxide ($H_2O_2$), 0.005M phosphate buffer, pH 7.00. This was prepared fresh from 30% $H_2O_2$ every day. Heavy metal contamination during preparation was avoided.
  2. 13 mg/ml sigma bovine liver catalase (Cat. #C-10). This was prepared fresh daily in distilled water. Catalase was stored on ice prior to use. The catalase was listed as having 1900 units/mg solid where 1 unit decomposes 1.0 $\mu$mole of $H_2O_2$ per minute at 25° C., while the $H_2O_2$ concentration falls from 10.3 to 9.2 $\mu$moles/ml in the reaction mixture.

B. Instrumentation
  A scanning ultraviolet spectrophotometer (Varian Associates) with constant temperature jackets around the sampling cuvettes was used.

C. Determination of Catalase Activity
  Catalase activity was measured via a U.V. assay. This assay follows the decrease in extinction of an $H_2O_2$ solution at 240 nanometers wavelength due to decomposition of $H_2O_2$ by catalase. See, generally, H. Äbi, "Catalase," in: Methods of Enzymatic Analysis, Vol. 2 ed. H. Bergmeyer, pp. 673–682 (1971), incorporated herein by reference.

1. Reaction Conditions
    a. pH 7.0, 0.005M phosphate buffer.
    b. Temperature=25° C.
  2. Procedure
    a. All assays were run against a 0.01M $H_2O_2$ blank (control) which was placed in the reference cell of the spectrophotometer.
    b. The reaction was initiated by adding 0.1 ml of catalase to 3.0 ml of 0.01M $H_2O_2$ in a quartz cuvette. The cuvette contents were mixed and placed into the spectrophotometer. The $A_{240}$ vs. time was monitored and the run was terminated as soon as the reaction began to deviate from linearity.

3. Calculations

Catalase activity was calculated in terms of sec.$^{-1}\mu\cdot g^{-1}$ over the linear range of reaction.

$$Activity = \frac{\ln\left(\frac{A_1}{A_2}\right)}{\left(\begin{array}{c}\mu g \text{ of catalase}\\ \text{in the reaction}\\ \text{mixture}\end{array}\right)\left(\begin{array}{c}\text{reaction}\\ \text{time}\end{array}\right)}$$

where $A_1$=Absorbance at time zero ($T_o$);

$A_2$=Absorbance at end of linear reaction; and reaction time=elapsed time from the beginning to the end of reaction linearity.

The assayed activity of Sigma bovine liver catalase used in the experiments portrayed in Example III was (9.8±0.7)× $10^{-4}$ $\mu g^{-1} sec^{-1}$ at pH 7.0, 25° C. in 0.01M hydrogen peroxide.

EXAMPLE III

Reaction Between Catalase and Hydrogen Peroxide

In a 40 ppm AO solution of $H_2O_2$ at pH 9.0, 21° C., 0.55 $\mu g/ml$ of catalase is required to decompose half of the active oxygen in 5.2 minutes (See Table I, below; FIG. 1). The A.O. level of the stock peroxide solution (without catalase) at the beginning and end of the experiment was 41 ppm. After 10 minutes incubation with 0.55 $\mu g/ml$ catalase, the AO dropped to 11 ppm. This was a significant decrease compared to initial AO and was clearly attributable to the catalase addition.

TABLE I

Effect of Catalase on $H_2O_2$

| Catalase Conc. ($\mu g/ml$) | Incubation Time (minutes) | ppm AO (x ± 2 standard deviations) |
|---|---|---|
| 0.00 | 0.0 | 41 ± 1 |
| 0.55 | 2.5 | 29 ± 1 |
| " | 5.0 | 21 ± 1 |
| " | 7.5 | 15 ± 1 |
| " | 10.0 | 11 ± 1 |
| 0.00 | 10.0 | 41 ± 1 |

The results of the incubations of peracetic acid and diperoxydodecanedioic acid (DPDDA) with catalase are depicted in Table II. Over a period of ten minutes, 0.55 $\mu g/ml$ of catalase did not alter the A.O. level of a 40 ppm solution of peracetic acid compared to controls. Even after raising the concentration of catalase to 38 $\mu g/ml$ and increasing the incubation time to 120 minutes, there was no significant difference between the initial A.O. and the A.O. following incubation with catalase.

The results for DPDDA were similar. At the end of 10 minutes incubation with 0.55 $\mu g/ml$ catalase, the A.O. level of a 12 ppm DPDDA solution did not drop when compared to controls. Over 120 minutes with 38 $\mu g/ml$ catalase, the A.O. level of the DPDDA solution dropped to 69% of original, while the A.O. level of the oxidant alone dropped to 72%. The difference in A.O. between the catalase-containing sample and the 120 minutes control was not statistically significant.

TABLE II

Reaction between catalase and peracids, pH 9.0, 21° C.

| Oxidant | Catalase Concentration ($\mu g/ml$) | Incubation Time (min) | % original A.O. (x ± 2 std. deviations) |
|---|---|---|---|
| Peracetic acid | 0 | 0 | 100 ± 3 |
| " | 0 | 10 | 96 ± 5 |
| " | 0 | 120 | 99 ± 0 |
| " | 0.55 | 10 | 101 ± 8 |
| " | 38.0 | 120 | 101 ± 5 |
| DPDDA | 0 | 0 | 100 ± 22 |
| " | 0 | 10 | 91 ± 3 |
| " | 0 | 120 | 72 ± 4 |
| " | 0.55 | 10 | 96 ± 7 |
| " | 38.0 | 120 | 69 ± 10 |

Table II demonstrates that catalase has little or no reactivity with peracid. In these data, there is no significant difference in the A.O. lost over the same times by catalase-spiked samples versus untreated samples.

From the foregoing, it is apparent that catalase is much more active against $H_2O_2$, which is its normal substrate, than against organic oxidants. As little as 0.55 $\mu g/ml$ catalase lower the A.O. level of a 40 ppm A.O. $H_2O_2$ solution by half in 5.2 minutes. On the other hand, catalase has little or no reactivity against the organic oxidants peracetic acid and DPDDA. From this discovery, Applicants determined to use catalase as a quenching agent for $H_2O_2$ in order to quantitate small amounts of organic oxidant versus a large background of $H_2O_2$.

In the following Example IV, the preferred effective amount of catalase was calculated. This was expressed as the catalase concentration needed to remove 800 ppm A.O. $H_2O_2$ from a 10 ml sample:

EXAMPLE IV 0.4 ml Sigma C100 catalase/50 ml aq. sol.=0.008 ml C100/ml $$\frac{0.008 \text{ ml C100}}{\text{ml}} \times 47.9 \text{ mg protein/ml C100} = 0.383 \text{ mg protein/ml}$$

0.383 mg protein'46,200 Units/mg protein=17.695 U/ml 17,695 U/ml × 0.5 ml/ 10.5 ml = 843 U/ml of sample Where U is 1 unit which catalyzes the decomposition of 1 micromole peroxide/minute as the concentration falls between 10.3 to 9.2 micromoles/ml.

In the following Example V, a protocol is demonstrated in which catalase is used as a quenching agent in solutions containing a known amount of previously generated peracid.

EXAMPLE V

In this example, the inventive concepts expressed in EP 253,487 and EP 268,452, were proofed. This concept can be expressed as the premise that esterolytic enzymes, e.g., lipase, will use peroxide rather than water in reacting with triglycerides and thus, form peracid. Since the preferred lipase/triglyceride reaction mixture is an emulsion, a method was developed capable of quantitating peracids in such emulsion. The reaction mixture contains equal parts of an oil (the glyceride)/water emulsion and water solution (containing lipase, buffer and bile salts (as an emulsifier)).

Instead, a single sample is split into two aliquots. One aliquot is used in an iodometric titration using a molybdate catalyst to quantitate the total A.O. from the generated peracid and $H_2O_2$. Catalase is added to the second aliquot to selectively scavenge $H_2O_2$, thus allowing the quantitation of peracid A.O. only. Peroxide A.O. was then calculated by subtracting peracid A.O. from total A.O.

In the following protocol, a model for determining peracid A.O. generated from lipase-mediated perhydrolysis was designed using preformed peracid.

Thus, the A.O. from DPDDA was determined in an olive oil/polyvinyl alcohol emulsion. Peracid A.O. was quantitated using catalase (3440 units of sigma bovine liver catalase per titration vessel). This was allowed to react for a minimum of 2 minutes before the reaction was stopped (and the peracid stabilized) by the addition of sulfuric acid. In the titrations with catalase, the endpoint was stable. This indicates that there was no peroxide available for reaction. The endpoint is also stable in the presence of molybdate catalyst. In solutions without catalase, unstable endpoints were observed, even in the absence of molybdate catalyst. This results from unreacted $H_2O_2$ in the titration mixture. The results are shown below:

TABLE III

| Sample | ppm A.O. peracid from DPDDA ± std. dev. |
| --- | --- |
| Water | 158 ± 0.1 |
| Emulsion | 140 ± 5 |

High levels of peracid were used to allow an initial observation of large and small effects.

In samples spiked with known levels of peracid, it was found that the emulsion gives lower A.O. values than water. This could be due to an A.O. loss from DPDDA instability in the emulsion.

EXAMPLE VI

Screening of Lipases for Enzymatic Perhydrolysis

Qualitative screening experiments for lipase-catalyzed perhydrolysis were begun using lipase from *Pseudomonas putida* sp. (see EP 268,456), Sigma, Miles PAN 250 and Novo 225 lipases. Reaction mixture contained the trioctanoin substrate, 1000 ppm A.O. ($H_2O_2$), 0.12M $HPO_4^{2-}$ at pH 11, and lipase. Equivalent control samples contained no enzyme. All samples were incubated at room temperature (about 21° C.) for 2 hours at which time catalase (700 $\mu$/ml) was added to eliminate A.O. contributed by $H_2O_2$. After 5 minutes incubation with catalase, an aliquot of the lipase solution was added to each control. Samples and controls were acidified and KI was added. The development of yellow color was observed visually but quantitation was impossible due to low oxidant levels produced (See Table IV below).

TABLE IV

| lipase (*Pseudomonas put.*) | Sigma lipase (*Candida cylinracea*) | Miles PAN 250 (porcine pancreas) | Novo 225 (mucor) |
| --- | --- | --- | --- |
| − | − | + | − |

A "−" indicates no yellow color development. The "+" in the table above, indicates that a yellow color was observed upon addition of KI, i.e. an oxidant was produced in incubation of Miles Pan 250 lipase at 0.5 mg/ml with trioctanoin/PVA substrate and $H_2O_2$. Peroctanoic acid is the most likely oxidant produced by this system.

EXAMPLE VII

Titration of Peracid and Peroxide

The A.O. of peroctanoic acid was measured in an emulsion containing 25% trioctanoin, 2% PVA (30:70 ratio of 78000:27000 mol. wts.) and water. The titration method used is based on a modification of the standard thiosulfate method for oxidants. In the standard titration, KI and sulfuric acid are added to the sample followed by immediate titration with thiosulfate. In this emulsion system, however, the triiodide species (which forms when iodide is oxidized) partitions into the emulsion phase where it is not accessible to the aqueous thiosulfate. To alleviate this problem, a dual solvent system (15 ml chloroform, 10 ml ethanol) was adopted which is added after the KI and sulfuric acid to allow the triiodide species to partition more readily into the aqueous phase of the reaction mixture.

Peracid and peroxide can be distinguished in the emulsion by using catalase. Catalase catalyzes the decomposition of hydrogen peroxide into water and oxygen. In this method samples are split into two aliquots: to the first, molybdate catalyst is added to allow the quantitation of the A.O. contributions of both peracid and peroxide; to the second, catalase is added to allow the quantitation of peracid only. The A.O. contribution of peroxide is calculated by subtracting the peracid A.O. from the total A.O.

The modified thiosulfate assay shows a linear response with increasing oxidant concentration in emulsion samples spiked with peroctanoic acid or hydrogen peroxide. This confirms that the amount of thiosulfate used in the titration is proportional to the amount of oxidant present over a range of oxidant concentrations and demonstrates that we have a working assay. Both peroctanoic acid and hydrogen peroxide were spiked into the emulsion to see if both species could be recovered from the same sample. The data listed below show that this method can distinguish between 20 and 1 ppm A.O. peracid with 100 ppm A.O. peroxide in the emulsion. As little as 0.66 ppm peracid can be qualitatively but not quantitatively observed in this particular experiment.

TABLE V

Recovery of Peracid and Hydrogen Peroxide in Lipase Substrate Emulsions.
Results are expressed in in ppm A.O.

| Example | Hydrogen Peroxide | | Peroctanoic Acid | |
| --- | --- | --- | --- | --- |
| | Titrated | Added | Titrated | Added |
| 1 | 99 | 101 | 19.6 | 19.7 |
| 2 | 99 | 100 | 16.0 | 20.1 |
| 3 | 90 | 93 | 17.2 | 18.0 |
| 4 | 105 | 100 | 2.0 | 1.84 |
| 5 | 97 | 92 | 2.2 | 2.2 |
| 6 | 105 | 101 | 1.6 | 1.1 |
| 7 | 94 | 101 | 1.2 | 1.3 |
| 8 | — | 103 | 0.0 | 0.66 |
| 9 | 93 | 101 | 1.2 | 0.77 |

In the next example, the effect of a different acidifying agent was observed. The type of acid is important in the titration to maintain an acidic pH so that $I_3^-$ can be titrated with thiosulfate.

EXAMPLE VIII

Acetic Acid as Acidifier

Air oxidation was previously observed when sulfuric acid used in the titration as an acidifier. Substitution of 20% acetic acid resolved this. Endpoint resolution was improved over the original chloroform/ethanol system by changing to a single phase titration system based on 40 ml of ethanol per 10 g of sample.

The experiments assembled in Table VI confirmed that the revised procedure is quantitative. Known amounts of peroctanoic acid and hydrogen peroxide were spiked into phosphate buffered trioctanoin/PVA emulsion (pH11) and titrated. Using the revised titration procedure, the peroctanoic acid and hydrogen peroxide originally spiked into the sample were recovered. The lower detection limit for peroctanoic acid lies between 1.4 and 0.6 ppm A.O. The limit, however, is probably not much below 1.4 ppm A.O. since the color of the peracid containing samples is nearly indistinguishable from the background color of the emulsion at 1.4 ppm A.O.

TABLE VI[1]

| ppm A.O. ± Standard Deviation | | | |
|---|---|---|---|
| Peroctanoic Acid | | Hydrogen Peroxide | |
| Titrated | Added | Titrated | Added |
| 13.8 ± 0.18 | 15.7 | 1120 | 1119 |
| 2.47 ± 0.14 | 2.29 | 1116 | 1124 |
| 1.76 ± 0.41 | 1.54 | 544 | 553 |
| 1.39 ± 0.12 | 1.27 | 564 | 559 |
| 0.58 ± 0.27 | 0.64 | 216 | 217 |
| | | 216 | 215 |
| | | 208 | 218 |
| | | 208 | 215 |

[1]The accuracy and precision of the revised thiosulfate titration method for peracid and hydrogen peroxide. Peroctanoic acid determinations were averages of 6 titrations.

The quantitative method was determined for peroctanoic acid. The error in the titration is 1.3% at 14 ppm A.O. and 8.6% at 1.4 ppm A.O. Throughout the range, however, the standard deviations remained relatively constant. The precision of the peroxide titration was not determined in this experiment.

Example IX

Automated Method for the Determination of Peracid and Peroxide in Trioctanoin/PVA Emulsions A. Materials
1. 0.01N Sodium Thiosulfate (J. T. Baker Dilute-it or equivalent)
2. Catalase (Sigma C-100 bovine liver, 40 kilo-units/mg protein, 43 mg protein/ml, 1 unit catalyzes the decomposition of 1 micromole peroxide/min as the peroxide concentration falls between 10.3 to 9.2 micromoles/ml.). Prepare 0.5 ml of catalase suspension in 50 ml of 0.1M phosphate, 0.01M NaCl, pH 7.0 buffer.
3. Molybdate catalyst
4. 20% Acetic Acid in deonized, distilled water
5. 10% Potassium Iodide (KI)-Solution is light sensitive and should be stored in a brown bottle under refrigeration until use
6. Ethanol B. Equipment
Metrohm AG CH-9100 Herisau Automatic titrator with Pt electrode and solenoids for the automatic addition of reagents. 20 ml buret.

C. Experimental
Two oxidant titrations were run on the enzymatic perhydrolysis reaction mixture: a) total active oxygen (total A.O) from hydrogen peroxide and peracid and b) peracid active oxygen. For the total A.O. titration, the sample is weighed out and acidified with 10 ml 20% acetic acid. Preliminary experiments indicate that immediate acidification of the samples improves the stability of the oxidants. This is important if titration of the samples is delayed.

Two drops of the molybdate catalyst solution are added to each sample to catalyze the reaction of hydrogen peroxide and $I^-$ to form $I_3^-$. $I_3^-$ is titrated with thiosulfate. Peracids also react with $I^-$ to produce triiodide, although this reaction does not require molybdate catalyst.

To perform peracid titrations, the hydrogen peroxide is removed from the perhydrolysis reaction mixture by reacting it with catalase to decompose the peroxide into water and oxygen gas. Again, catalase was found not to decompose peracids. 0.5 ml of 2.0N HCl is added to perhydrolysis samples at pH 11.0. Samples at pH 7.5 need not be acidified. 2-1 ml aliquots of the catalase stock solution added 4 minutes apart are sufficient to decompose 1000 ppm A.O. hydrogen peroxide in a 10 g sample of the perhydrolysis reaction mixture. In this example, it was found that the amount of catalase used, in activity units was 3688 U/ml, calculated as follows:

0.5 ml/50 ml Sigma C100 catalase/50 ml aq. sol.=0.01 ml C100/ml 0.01 ml C100/ml×47.9 mg protein/ml C100=0.479 mg protein/ml 0.479 mg protein/ml×46,200 Units/mg protein=22.129 U/ml 22,129 U/ml×2 ml/12 ml = 3688 U/ml of sample Where U is 1 unit which catalyzes the decomposition of 1 micromole peroxide/minute as the concentration falls between 10.3 to 9.2 micromoles/ml.

Following catalase incubation, samples are acidified with 10 ml of 20% acetic acid. To test for complete decomposition of hydrogen peroxide, molybdate is added to one of the replicate samples: if the molybdate treated sample shows higher A.O. levels then its untreated counterpart, then the catalase incubation is not complete.

In an alternative technique, prior to titration, 837 U/ml catalase was added to the 10 ml samples containing trioctanoin/PVA emulsion. Immediately afterwards, approximately 10 ml $H_2O$ is forcibly added in a downward stream to double the sample volume (the volume of the water addition is not critical since only $I_3^-$ is titrated). Surprisingly, using such relatively small amount of catalase in conjunction with the water stream resulted in an immediate reaction with the catalase, since a gas was observed to evolve. It is believed that this alternate technique of dispersing catalase into the sample resulted in a complete decomposition of $H_2O_2$. This may be the result of a degassing of the sample when the water stream was introduced, although there may be equally plausible mechanisms known to those skilled in the art, which may be responsible.

Figure 2:
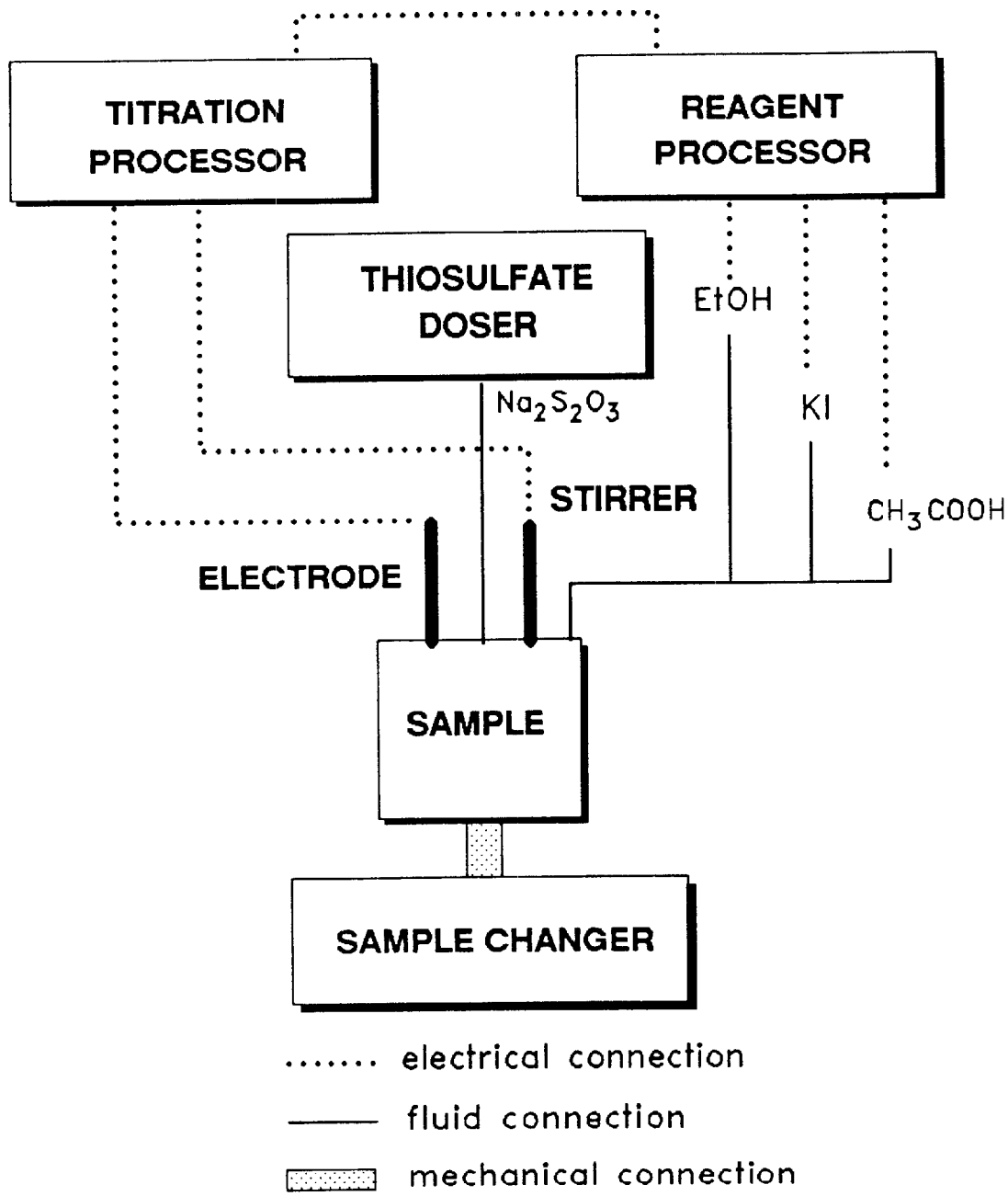
FIG. 2 is a schematic depiction of an automated peracid titration system of the invention.

The Metrohm autotitrator is depicted in FIG. 2. It comprises a titration processor, a thiosulfate (titrant) autoburet, and three reagent ports controlled by solenoids. Thus, four solutions dispense into the reaction vessel or sample container. In this system, solenoid #1 dispenses 25 ml of ethanol into the reaction vessel to break and dilute the emulsion. Solenoids #2 and #3 dispense 10 ml of KI and acetic acid, respectively. Titration with thiosulfate follows after which solenoid #4 dispenses 50 ml of water to clean the electrode, stirrer, and reagent dispensing probe. Samples are introduced via sample changer, which rotates samples and centers them under the electrode and stirrer, which are lowered into, and lifted out of, the sample container.

The titration processor was programmed in the controlled drift kinetics mode (45(mV/min) with a high (1) measuring point density. The number of endpoints per titrations was limited to 1 and the number of buret volumes used per titration was limited to 3. The instrument displays mV readings between 0 and 300 mV. The other parameters were left at their default values.

The instrument was programmed to calculate ppm active oxygen (A.O.) using the volume of 0.01N thiosulfate dispensed and the sample weight. On the Applicants' instrument, the sample weight is read into the Metrohm's memory using an interfaced balance. The calculation is shown below:

$$\text{ppm A.O.} = \frac{(\text{ml thiosulfate})(N \text{ thiosulfate})(8000)}{\text{sample wt (g)}}$$

EXAMPLE X

Peracid Production by Lipases in Trioctanoin/PVA Emulsions

A. Preparation of the Substrate Emulsion

1. Reagents—All solutions are prepared in deionized, distilled water.
    a. Tricaprylin-Sigma #T-9126 Grade II, 90%+purity
    b. Polyvinyl alcohol-Air Products (PVA) Vinol 325 77–79K MW
    c. Polyvinyl alcohol-Air Products (PVA) Vinol 107 22–31K MW
2. Equipment
   a. Braun Sonic-2000 Sonicator
   b. Ice bath
   c. Thermometer 3. Experimental:

PVA is prepared in water; the total concentration of PVA in the stock solution is 2% w/v using a 30:70 ratio of Vinol 325 to Vinol 107. The mixture is heated to 85° C. until all of the PVA is fully dissolved. The solution is allowed to cool and trioctanoin added at 25% v/v. The mixture is sonicated for 10 min. using a Braun Sonic 2000 Sonicator set at 370 watts (measured on the instrument's power meter). The temperature of the emulsion was kept below 30° C. during the sonication by setting the emulsion mixture in an ice/brine bath. Using this procedure, uniform emulsion is produced in up to 1 liter volumes. Emulsion produces stable lipase activities for up to 2 weeks if stored in a sealed container under refrigeration.

Using the protocols established in Examples VIII and IX, peracid A.O. generated by lipolytic perhydrolysis and proteolytic perhydrolysis was quantitated in Tables VII–XII below. The data in these tables are from copending U.S. applications Ser. No. 07/363,442, (filed Jun. 6, 1989, a continuation of Ser, No. 06/872,252, filed Jun. 9, 1986, now abandoned); which was succeeded by Ser. No. 07/768,466, filed Sep. 30, 1991, now abandoned, itself succeeded by Ser. No. 07/964,565, filed Oct. 21, 1992, now U.S. Pat. No. 5,296,161; Ser. No. 06/932,717, (filed Nov. 19, 1986) now U.S. Pat. No. 5,030,240 and Ser. No. 07/243,331 (filed Sep. 12, 1988), which was succeeded by Ser. No. 07/697,534, filed Apr. 30, 1991, now abandoned itself succeeded by Ser. No. 07/954,438, filed Sep. 30, 1992, now U.S. Pat. No. 5,364,554 all of which are incorporated herein by reference.

In Table VII below, perhydrolysis screening studies were conducted for a number of different commercially available lipolytic enzymes. The reaction conditions were 12.5 wt. % trioctanoin as a glyceride substrate, polyvinyl alcohol as an emulsifying agent in a concentration of 70:30 mixture of 28,000 mol. wt. and 77,000 mol. wt., and $H_2O_2$ at a concentration of about 400 ppm A.O. at room temperature, and a pH of 9.0. The inventive quantitation method was able to determine quantitatively whether the studied lipases were actually able to generate peracid, and in what amount.

TABLE VII

Screening Study of Various Commercial Lipases for Peracid Generation

| | Enzyme | | | Enz. Con. | Hydrls. rate | Peracid |
|---|---|---|---|---|---|---|
| Eg. | Commerc. Name | Organism | Supplier | (mg/ml) | (meq/min) | ppm A.O. |
| 1. | Lipase K | *Aspergillus niger* | Amano | 1.0 | 0.5 | 1.4 |
| 2. | Lipase Type VI | *Candida cylindracea* | Sigma | 1.0 | 0.2 | 1.3 |
| 3. | " | " | " | 3.0 | 1.7 | 1.9 |
| 4. | CES Lipase | *Pseudomonas fl.* | Amano | 1.0 | 1.0 | 1.3 |
| 5. | Enzeco Conc. | *Candida cylindracea* | Enz. Dev. | 1.0 | 0.05 | 1.5 |
| 6. | " | " | " | 10.0 | 0.2 | 2.3 |
| 7. | Lipase S | Rhizopus sp. | GB | 1.0 | 1.5 | 0.7 |
| 8. | " | " | " | 0.2 | 0.8 | 1.0 |
| 9. | Lipase P | Pseudomonas sp. | Amano | 1.0 | 0.6 | 1.1 |
| 10. | Enzeco Pan | Mammal | Enz. Dev. | 1.0 | 0.4 | 0.9 |
| 11. | Lipase AIE | *Aspergillus niger* | Amano | 1.0 | 0.03 | 0.9 |
| 12. | " | " | " | 5.0 | 0.14 | NP |
| 13. | Lipase 2212F | Fungal | Rohm Enz. | 1.0 | 0.2 | 0.8 |
| 14. | " | " | " | 3.0 | 1.5 | 2.2 |
| 15. | Lipase JV | *Rhizopus jav.* | Amano | 1.0 | 2.2 | 0.8 |
| 16. | " | " | " | 5.0 | 1.9 | 1.2 |
| 17. | Lipase A | Alcaligenes sp. | Enz. Dev. | 1.0 | 0.3 | 0.8 |
| 18. | Fermlipase PL | Mammal | Fermco | 1.0 | 0.6 | 0.8 |
| 19. | Pancreatic (pure) | Pig | U.S. Bio. | 1.0 | 0.3 | 0.8 |
| 20. | Pancreatic (crude) | Pig | U.S. Bio. | 1.0 | 0.1 | 0.7 |

TABLE VII-continued

Screening Study of Various Commercial Lipases for Peracid Generation

| Eg. | Enzyme Commerc. Name | Organism | Supplier | Enz. Con. (mg/ml) | Hydrls. rate (meq/min) | Peracid ppm A.O. |
|---|---|---|---|---|---|---|
| 21. | Pancreatic (crude) | Pig | " | 5.0 | 1.5 | NP |
| 22. | Lipase 2212C | Pig | Rohm Enz. | 1.0 | 0.5 | 0.7 |
| 23. | Sigma Type XI | *Rhizopus Arrhizus* | Sigma | 0.006 | 5.4 | 1.4 |
| 24. | " | " | " | 0.003 | 2.8 | 1.5 |
| 25. | Lipase SP 285 | Fungal | Novo | 1.0 | 1.5 | NP |
| 26. | Lipase 2212E | Fungal | Rohm Enz. | 1.0 | 0.3 | NP |
| 27. | " | " | " | 5.0 | 1.3 | NP |
| 28. | Lipase CV | Microbial | Fermco | 1.0 | 1.1 | NP |
| 29. | Novozym 225 | *Mucor meithei* | Novo | 1.0 | 0.4 | NP |
| 30. | Lipase MAP | Muco sp. | Amano | 1.0 | 0.3 | NP |
| 31. | " | " | " | 10.0 | 3.0 | NP |
| 32. | Palatase | *Aspergillus niger* | Novo | 1.0 | NH | NP |
| 33. | " | " | " | 10 | NH | NP |
| 34. | " | " | " | 0.2 | 0.9 | NP |
| 35. | Lipase B | *P. nitroreducens* | Amano | 1.0 | 1.5 | NP |
| 36. | Lipase LP | *Chromobacterium viscosum* | Toyo Jozo | 1.0 | 3.6 | NP |
| 37. | " | *Chromobacterium viscosum* | " | 0.2 | 0.9 | NP |
| 38. | Lipase 300 | Pregastric goat | Miles | 1.0 | NH | NP |
| 39. | " | " | " | 10 | NH | NP |
| 40. | Lipase 400 | Pregastric kid | Miles | 1.0 | NH | NP |
| 41. | " | " | " | 10 | NH | NP |
| 42. | Lipase 600 | Pregastric calf | Miles | 1.0 | NH | NP |
| 43. | " | " | " | 10 | NH | NP |
| 44. | Pan 250 | Pig pancreas | Miles | 1.0 | 0.4 | NP |
| 45. | Lipase Type II | Pig Pancreas | Sigma | 1.0 | 0.5 | NP |

In shown in Example XI and Table VIII, an experimental lipase derived from *Pseudomonas putida* sp. was tested for perhydrolysis. The enzyme, as described in EP 268,456 and U.S. Ser. No. 06/932,717, filed Nov. 19, 1986, now U.S. Pat. No. 5,030,240 both of which disclosures are incorporated herein by reference, was derived from the described bacterium deposited at the American Type Culture Collection, Rockville, Md., under ATCC 53552.

EXAMPLE XI

After the lipase (designated lipase 1) was cultured in a fermentation broth, it was partially purified by DEAE Sephacryl chromatography followed by Sephadex G-100 gel permeation chromatography. A DEAE column was equilibrated in 10 mM sodium phosphate buffer, pH 8, and the crude protein was applied to the column in the same buffer. PNB (p-nitrophenyl butyrate) hydrolase activity that was not bound to the column was associated with lipase 1. Lipase 1 thus obtained from the DEAE step was subjected to chromatography on Sephadex G-100 in 10 mM sodium phosphate buffer at pH8. Lipase 1 eluted from this column as a discrete peak, and was identified by PNB hydrolase activity as well as perhydrolytic activity, as shown below.

The enzyme preparation as in Example XI was screened for perhydrolysis and compared against two commercially available enzymes. The perhydrolysis screening used 0.5 wt. % SDS as an emulsifier. Each test sample had 480 ppm $H_2O_2$, enzyme at 6/4 g/ml, trioctanoin substrate at 5 wt. % and 0.5 wt. % SDS. The constant pH was 10 and the temperature was 25° C. Table VIII sets out the perhydrolysis profile for this enzyme.

TABLE VIII

| Time (min.) | Peracid generated (ppm A.O.) |
|---|---|
| 2 | 3.9 |
| 4 | 7.2 |
| 6 | 8.1 |
| 8 | 9.0 |
| 10 | 9.9 |

By contrast, the amount of peracid generated with commercially available Lipase CES (said to be derived from *Pseudomonas fl.,* available from Amano) remained substantially constant and low (about 0.5 ppm A.O. peracid), while the amount of peracid generated by commercially available Lipase K remained substantially constant and even lower (about 0.3 ppm A.O. peracid).

In Tables IX–XII below, perhydrolysis screening studies were conducted for a number of different commercially available protease and esterolytic enzymes. These examples also showed that the inventive quantitation method was able to determine quantitatively whether-the studied enzymes were actually able to generate peracid, and in what amount.

In Table IX, various enzymes were employed in combination with methylacetate as a substrate for producing peracid in the presence of the enzyme and $H_2O_2$, in an aqueous solution at pH 10.5. Example 7 of Table IX shows a run at pH 8.5, but did not show perhydrolysis. The perhydrolysis examples of Table IX were run in an aqueous solution on a pH stat (30 ml sample size) with 400 ppm A.O. $H_2O_2$.

TABLE IX

| Eg. | Enzyme | Total Enzyme Activity[2] | pH | Perhydrolysis[1] ppm peracid AO |
|---|---|---|---|---|
| 1. | (control) | — | 10.5 | not sig.[3] |
| 2. | Esperase | 11.5 U | 10.5 | 0.92(0.03) |
| 3. | Alcalase | 4.4 mU | 10.5 | 0.93(0.06) |
| 4. | Alpha-Chymotrypsin | 138 U | 10.5 | 0.83(0.02) |
| 5. | Alpha-Chymotrypsin | 276 U | 10.5 | 0.72(0.04) |
| 6. | Carboxypeptidase A | 2.7 U | 10.5 | 0.92(0.10) |
| 7. | Carboxypeptidase A | 2.7 U | 8.5 | 0.92(0.10) |

[1] all peracid A.O. data includes the standard deviation reported in parenthesis. The standard deviation is defined by the following formula:

$$s = \sqrt{\frac{\sum (X - \overline{X})^2}{n - 1}}$$

where the term $\Sigma(X-\overline{X})^2$ is the sum of the squares of the deviations from the mean and "n" is the sample size.
[2] Activity units for the enzymes were defined as follows:
Esperase: 3.83 KNPU/g
Alcalase: 1.48 Anson unit/g
Carboxypeptidase: 892.9 U/ml
Alpha-Chymotrypsin: 46 U/mg solid
The total refers to enzymatic activity in the perhydrolysis samples. See also U.S. Ser. No. 07/243,331, filed September 12, 1988, page 14, which was succeeded by Ser. No. 07/697,534, filed April 30, 1991, now abandoned, itself succeeded by Ser. No. 07/954,438, filed September 30, 1992, now U.S. Pat. No. 5,364,554 incorporated herein by reference.
[3] not significant (relative to error as measured by standard deviation.

Table X below demonstrates similar results for generally the same enzymes used with methylmethoxyacetate as the substrate. The reaction conditions described for the examples of Table IX were repeated. Multiple examples for each enzyme assayed are displayed because of the differing levels of perhydrolysis.

TABLE X

| Eg. | Enzyme | Total Enzyme Activity[2] | Perhydrolysis[1] ppm peracid AO |
|---|---|---|---|
| 1. | (control) | — | not. sig.[3] |
| 2. | Esperase | 11.5 U | 1.5(0.1) |
| 3. | Alcalase | 4.4 mU | 1.6(0.0) |
| 4. | " | 2.2 mU | 1.6(0.2) |
| 5. | " | 1.1 mU | 1.6(0.0) |
| 6. | " | 0.6 mU | 1.3(0.1) |
| 7. | Alpha-Chymotrypsin | 138 U | 1.5(0.0) |
| 8. | " | 69 U | 1.7(0.1) |
| 9. | " | 35 U | 1.7(0.0) |
| 10. | " | 17 U | 1.7(0.0) |
| 11. | Carboxypeptidase | 22 U | 1.3(0.0) |
| 12. | " | 9 U | 1.4(0.0) |
| 13. | Carboxypeptidase (+0.5M NaCl) | 22 U | 1.5(0.1) |
| 14. | Carboxypeptidase (+0.5M NaCl) | 9 U | 1.0(0.1) |

[1] Same as in Table IX, above.
[2] Same as in Table IX, above.
[3] Same as in Table IX, above.

In the examples of Table XI below, a number of enzymes were screened for perhydrolysis using, as a substrate, (2-hexyloxyethoxy)acetic acid, (2-hydroxypropyl)ester (6.25 mM, 0.188 meq.). The reactions were carried out in an aqueous solution on the pH stat (30 ml samples) at a constant pH of 10.5, 400 ppm A.O. $H_2O_2$. Again multiple examples for some enzymes are reported.

TABLE XI

| Eg. | Enzyme | Total Enzyme Activity[2] | Perhydrolysis[1] ppm peracid AO |
|---|---|---|---|
| 1. | (control) | — | 3.3(0.6) |
| 2. | Esperase | 11.5 U | 3.5(0.1) |
| 3. | Alcalase | 4.4 mU | 3.9(0.0) |
| 4. | " | 0.4 mU | 4.1(0.1) |
| 5. | Alpha-Chymotrypsin | 138 U | 3.7(0.0) |
| 6. | " | 14 U | 4.0(0.0) |
| 7. | Carboxypeptidase A | 89 U | 4.1(0.0) |

[1] Same as in Table IX, above.
[2] Same as in Table IX, above.

In Table XII, 2-hydroxypropyloctanoate was the substrate. The reaction conditions stated for Table IX, above, were repeated.

TABLE XII

| Eg. | Enzyme | Total Enzyme Activity[2] | Perhydrolysis[1] ppm peracid AO |
|---|---|---|---|
| 1. | (control) | — | 0.44(0.1) |
| 2. | Esperase | 11.5 U | 0.51(0.01) |
| 3. | " | 1.15 U | 0.57(0.02) |
| 4. | Alcalase | 4.4 mU | 0.56(0.01) |
| 5. | " | 0.4 mU | 0.42(0.01) |
| 6. | Alpha-Chymotrypsin | 138 U | 0.85(0.02) |
| 7. | " | 14 U | 0.59(0.02) |
| 8. | Carboxypeptidase | 18 U | 0.54(0.01) |

[1] Same as in Table IX, above.
[2] Same as in Table IX, above.

From the above, it can be seen that the invention provides a proficient method for quantitating organic oxidants in presence of a relatively large quantity of hydrogen peroxide. The quantitative method can be used both for the products of enzymatic and chemical perhydrolysis. However, It is to be understood that this invention is not limited to these examples, and may apply to all speciation of oxidants and associated detection/quantitation methods. The invention is further illustrated by reference to the claims which follow below, although obvious embodiments and equivalents are covered thereby.

What is claimed is:

1. A method for quantitating an organic peracid comprising:
   introducing, into a sample solution containing an organic peracid in the presence of a high background of hydrogen peroxide in said solution, an amount of catalase sufficient to decompose said hydrogen peroxide in said solution;
   reacting all of the hydrogen peroxide present in said solution with sufficient amount of said catalase without decomposing said organic peracid present in the solution; and
   quantitating said organic peracid in ppm active oxygen (A.O.) by measuring an amount of said organic peracid in an absence of said hydrogen peroxide.

2. The method of claim 1 wherein said organic peracid is a perhydrolysis reaction product of a source of hydrogen peroxide and an organic activator for said source of hydrogen peroxide.

3. The method of claim 2 wherein said organic activator is a surface active compound.

4. The method of claim 2 wherein said organic activator further comprises a reaction product of lipase and a substrate therefor, which, in the presence of hydrogen peroxide, generates peracid enzymatically in an amount as low as 0.3 ppm A.O.

5. The method of claim 4 wherein said substrate is an ester and said enzyme is lipase.

6. The method of claim 5 wherein said ester is selected from the group consisting of:
(i) glycerides having the structure

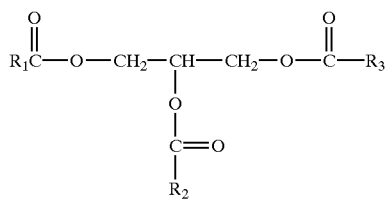

wherein $R_1 = C_1$-$C_{12}$ alkyl, $R_2 = C_1$-$C_{12}$ alkyl or H and $R_3 = C_1$-$C_{12}$ alkyl or H;

(ii) ethylene glycol derivatives having the structure

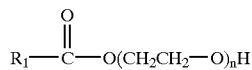

wherein $n = 1$–$10$ and $R_1$ is defined as above; and (iii) propylene glycol derivatives having the structure

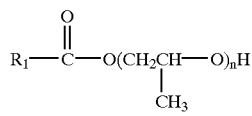

wherein $R_1$ and n are defined as above.

7. The method of claim 1 wherein said solution is acidified with an inorganic or organic acid after said catalase has been introduced.

8. The method of claim 7 wherein said acid is sulfuric acid.

9. The method of claim 7 wherein said acid is acetic acid.

10. The method of claim 1 wherein the quantitating step comprises contacting the organic, peracid with an oxidizable reagent to form a detectable product.

11. The method of claim 10 wherein said detectable product is a colored product.

12. The method of claim 11 wherein said reagent is potassium iodide.

13. The method of claim 12 comprising contacting said solution with a titrant which will react with said reagent to decolorize the colored product.

14. The method of claim 13 wherein said titrant is sodium thiosulfate.

15. The method of claim 14 wherein sodium thiosulfate titrated is used to quantify the oxidant present.

16. The method of claim 10 wherein said detectable product is quantitated by potentiometric quantitation.

17. The method of claim 16 wherein said potentiomtric quantitation is automated.

18. The method of claim 1 wherein the amount of catalase is the number of units that, for a 10 ml sample; of $H_2O_2$ (800 ppm A.O.), will completely decompose, oxidize or quench the $H_2O_2$ within three minutes at room temperature (about 21° C.) at a pH of about 10.5, without substantially affecting any peracid present in the sample.

19. The method of claim 1 wherein the introducing step is followed by an rapid introduction of a liquid which does not participate in the perhydrolysis reaction.

20. The method of claim 19 wherein the liquid is water.

* * * * *